United States Patent [19]

Stille

[11] Patent Number: 4,870,344
[45] Date of Patent: Sep. 26, 1989

[54] METHOD FOR INSPECTING INTEGRATED CIRCUITS OR OTHER OBJECTS

[75] Inventor: Göran Stille, Sollentuna, Sweden

[73] Assignee: Stiftelsen Institutet for Mikrovagsteknik Vid Tekniska Hogskolan I Stockholm, Stockholm, Sweden

[21] Appl. No.: 729,756

[22] Filed: May 2, 1985

[30] Foreign Application Priority Data

May 9, 1984 [SE] Sweden ............................... 8402518

[51] Int. Cl.⁴ ...................... G01N 23/00; G01R 31/28
[52] U.S. Cl. ............................ 324/73 R; 324/158 R; 324/158 D; 250/310; 250/311
[58] Field of Search ............ 324/73 R, 158 R, 73 PC, 324/158 D; 250/310, 491.1, 311; 356/398, 394, 401; 364/513, 815, 731

[56] References Cited

U.S. PATENT DOCUMENTS

| 3,207,904 | 9/1965 | Heinz | 324/158 D |
|---|---|---|---|
| 4,220,854 | 9/1980 | Feuerbaum | 250/310 |
| 4,277,679 | 7/1981 | Feuerbaum | 324/158 D |
| 4,318,003 | 3/1982 | Ono et al. | 356/401 |
| 4,413,181 | 11/1983 | Feuerbaum | 324/158 D |
| 4,413,186 | 11/1983 | Uema | 250/491.1 X |
| 4,420,691 | 12/1983 | Zasio | 250/491.1 X |
| 4,558,225 | 12/1985 | Gotou et al. | 250/491.1 X |
| 4,581,534 | 4/1986 | Todokoro et al. | 324/158 D |
| 4,613,943 | 9/1986 | Miyake et al. | 364/513 X |
| 4,636,968 | 1/1987 | Gotou et al. | 250/491.1 X |

Primary Examiner—Reinhard J. Eisenzopf
Assistant Examiner—Vinh P. Nguyen
Attorney, Agent, or Firm—Nies, Webner, Kurz & Bergert

[57] ABSTRACT

A method for inspecting integrating circuit or other objects, in which the object is irradiated with an electron beam and in which a detector is caused to detect electrons emitted from the object, to determine the voltage level of the object or some other property at one or more points, or another signal generated upon irradiation. The points or nodes on the object to be inspected are allocated coordinates $(x'_i, Y'_i)$ in a coordinate system x'-y' related to the object where identification points on the object are determined or applied to the object, these identification points also being allocated coordinates $(x'_i, y'_i)$. The object is placed in an electron-microscope type apparatus, where the position of the coordinate system x'- y' in relation to a coordinate system x - y related to the electron microscope is determined, by determining the positions of the identification points relative to the coordinate system x - y. The electron beam is then deflected and brought into alignment with and caused to irradiate the points or nodes in successive order, the detector output signal obtained when irradiating each of the selected points or nodes being compared with a pre-determined value for each such point.

8 Claims, 1 Drawing Sheet

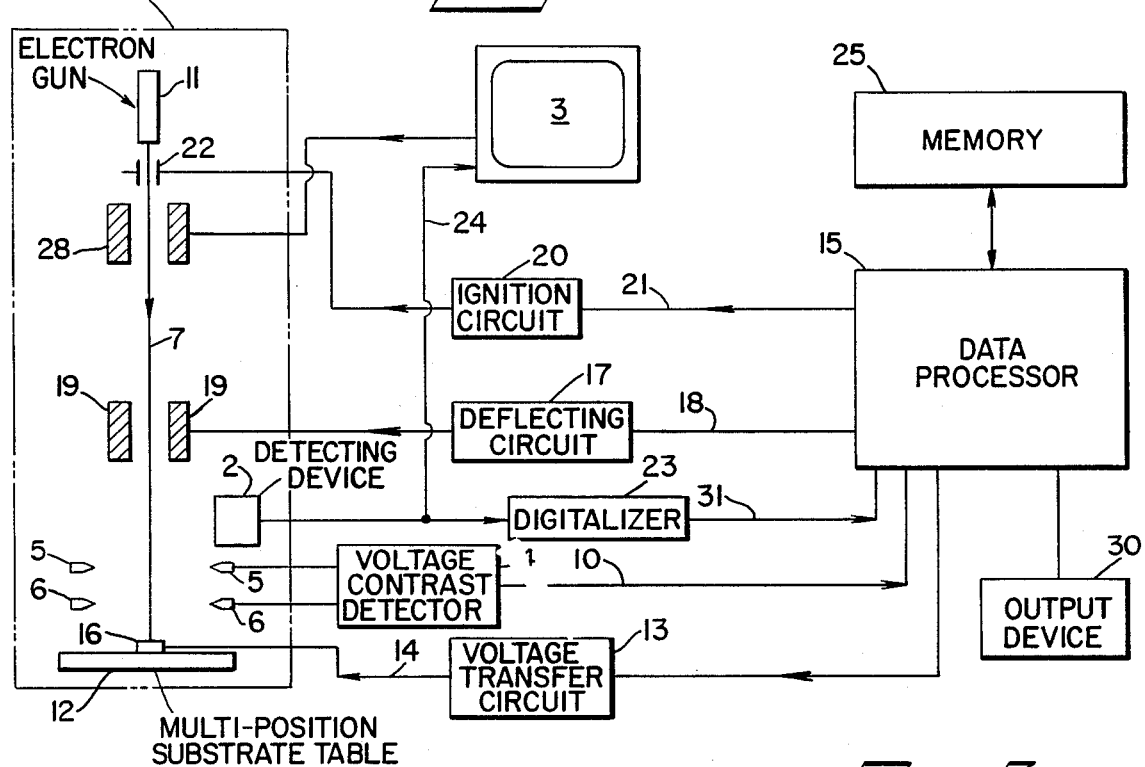
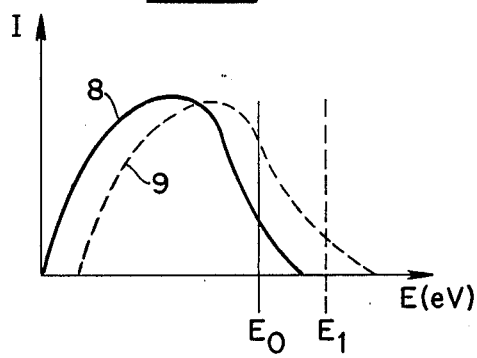
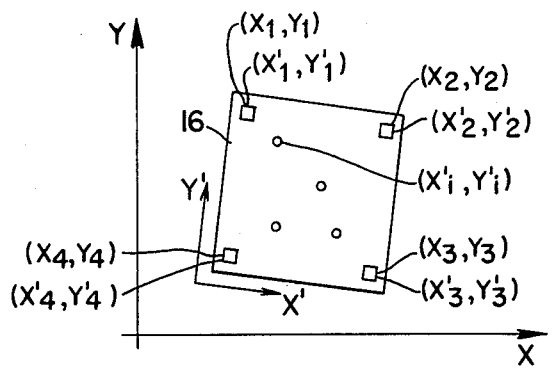
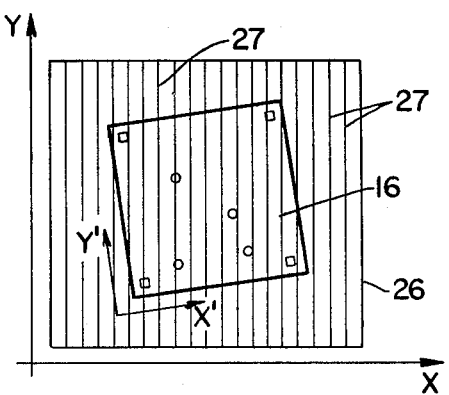

METHOD FOR INSPECTING INTEGRATED CIRCUITS OR OTHER OBJECTS

The present invention relates to a method for inspecting integrated circuits or other objects.

Integrated circuits incorporate a particularly large quantity of electronic components mounted on a substrate. Because of the complexity of these circuits and their extremely small geometrical dimensions, the task of inspecting such circuits is both troublesome and time-consuming.

There is a great need for ways and means which enable integrated circuits to be inspected, and therewith checked, in the various stages of their manufacture. This need relates partly to the inspection of such circuits in certain stages of their manufacture, partly the inspection of randomly selected completed circuits, and partly the inspection of all circuits manufactured in a given context. In conjunction with the development of integrated circuits, there is also a need to scan or sense and inspect various components in different parts and points on the circuits.

The cost of inspecting an integrated circuit and the difficulties encountered when making the inspection will naturally increase with the complexity of the circuits. When applying conventional techniques, the cost of the inspection begins to exceed the costs of production up to the stage at which the inspection commences.

In one known method for monitoring integrated circuits the voltage in the inner nodes of the circuit is measured with the aid of an electron beam. When applying this known method, the circuit is placed in an electron microscope equipped with a voltage-contrast recorder. A voltage is applied to the outer terminals of the integrated circuit, such that certain nodes of the integrated circuit obtain a voltage level above a given value, while other nodes of the circuit obtain a voltage level below a given value.

The integrated circuit is then displaced mechanically to a position in which the electron beam of the electron beam microscope impinges on the node which is normally a conductor in the circuit and the voltage level of which it is desired to know. In dependence on the voltage level of the node there is generated an energy spectra which is sensed by the voltage-sensitive detector This enables the voltage level of a node in the circuit to be measured.

The circuit is then displaced mechanically to a position in which the next node is irradiated with the electron beam and the node is investigated, whereafter the circuit is again displaced, and so on. The time between each displacement is from 1 to 10 seconds.

It is obvious that it is impossible to inspect an integrated circuit comprising 100,000 or more nodes, or when the circuit has to be positioned manually is extremely time-consuming and laborious.

The present invention affords a solution to this difficult problem and provides a method by means of which a particularly large number of nodes can be examined per unit of time.

The present invention relates to a method for inspecting integrated circuits or other objects, in which the object is irradiated with an electron beam and in which a detector is caused to detect electrons emitted from the object, to determine the voltage level of said object or some other property thereof at one or more points, or to detect some other signal generated when irradiating the object, and is characterized in that the points or nodes on the object to be inspected are given coordinates in a coordinate system $x' - y'$ related to the object; in that identification points on the object are determined or are applied to the object, these identification points also being given coordinates; in that the object is placed in an electron-microscope type apparatus; in that the position of the coordinate system $x' - y'$ relative to a coordinate system $x - y$ related to the electron microscope is determined by determining the position of the identification points relative to the coordinate system $x - y$; in that the electron beam is then deflected onto and caused to irradiate said points or nodes in a successive order; and in that when irradiating each of the selected points or nodes, the detector output signal obtained therewith is compared with a given value for each such point.

The invention will now be described in more detail with reference to an embodiment thereof illustrated in the accompanying drawing, in which FIG. 1 is a block schematic of an arrangement by means of which the present invention can be carried out;

FIG. 2 is a diagram, the nature of which is described hereinafter;

FIGS. 3 and 4 illustrate an integrated circuit incorporated in two coordinate systems.

FIG. 1 is a block schematic of an arrangement by means of which the present method can be carried into effect.

In FIG. 1 the reference 1 identifies a conventional electron microscope, suitably a scanning electron microscope. Those devices embodied in an electron microscope have not been shown in complete detail in FIG. 1, since such devices are known and do not form any part of the present invention. An electron microscope manufactured by Philips and designated 505 constitutes an example of those electron microscopes which can be used in this context.

The reference 2 identifies a detecting or sensing device, while the reference 3 identifies a presentation screen of conventional design in electron microscopes. The image is produced by re-emission of electrons from a scanning electron beam.

The electron microscope incorporates a voltage-constrast detector 4 including, for example, annular electrodes 5, 6. The detector 4 is suitably of known kind. A detector of the make LINTECH may be used, for example. This detector is arranged to sense the secondary emission of electrons from an object irradiated with an electron beam 7. The detector 4 is arranged, when detecting electrons above a given energy level ($E_o$), to produce an output signal in relation to the voltage prevailing at the point sensed. An example of energy spectra is illustrated in FIG. 2. The diagram of FIG. 2 exhibits two curves, a full-line curve 8 and a broken-line curve 9. The full-line curve 8 can be obtained when a node of an integrated circuit irradiated by the electron beam has a given potential. If the node has a lower electrical potential, the curve is displaced towards a higher energy, as illustrated by the broken-line curve 9. Consequently, by measuring the quantity of electrons having an energy level above a given energy level ($E_o$) it is possible to establish whether the electric potential in a node is above or beneath a pre-determined level.

The detector 4 is adapted to determine the energy level $E_o$, $E_1$, over which the surface beneath the curve has a given value.

The energy level recorded when inspecting a node is suitably analogue/digital converted, so that there is obtained on the output 10 of the detector 4 a digitalized signal containing information concerning the potential of the node in question.

Since the detector 4 and associated electrodes 5, 6 are commercially available and do not form any part of the present invention, they will not be described in further detail.

The electron beam 7 can either be generated by the electron gun 11 of the electron microscope or by one or more separate electron guns, not shown. The reference 12 identifies a multi-positional substrate table of the kind found in electron microscopes.

The reference 13 identifies a conventional circuit adapted to apply voltage to the outer terminals of an integrated circuit via conductors 14. The circuit 13 is adapted to apply voltage in accordance with different patterns and sequences in response to instructions given by a data processor 15.

In accordance with the present invention devices are used for identifying the position of an integrated circuit 16 in an x - y plane substantially perpendicularly to the direction of the electron beam, and also devices operative to deflect the electron beam to sense pre-determined nodes ($x'_i$, $y'_i$), subsequent to identifying the position of the circuit 16.

The coordinate system x - y in FIGS. 3 and 4 identifies a coordinate system related to the electron microscope. The coordinate system x' - y' identifies a coordinate system related to the integrated circuit 16.

The arrangement also incorporates a deflecting circuit 17 which is controlled by the data processor 15, through conductors 18, and adapted to control one or more devices 19 for deflecting the electron beam 7. The deflecting devices 19 may be magnetic and/or electrostatic. For the purpose of deflecting the beam rapidly with high precision, the deflecting devices are arranged in or after the last part of the electron lens system. There is also provided an ignition circuit 20 which is adapted to be controlled by the data processor 15, through conductors 21, and to ignite and to extinguish the electron beam 7, through means 22.

In accordance with the present invention there is selected a number of nodes which are to be inspected with regard to their electrical potential. The coordinates of the nodes are determined in the coordinate system x' - y' and allotted the coordinates ($x'_i$, $y'_i$, in which i=5, 6, 7 . . . . . , n. The integer n can reach to 100,000 or more.

Three or more identification points ($x'_i$, $y'_i$), ($x'_2$, $y'_2$), ($x'_3$, $y'_3$) and ($x'_4$, $y'_4$) constituting reference points in the circuit are selected. These points may comprise points of characteristic appearance or may comprise points purposely placed on the circuit. It is essential that the points can be identified, either from their appearance or through the voltage obtained when the voltage applying circuit 13 applies voltage to the integrated circuit 16 in a given manner, or some other signal produced when irradiating the points.

When carrying out the method, an integrated circuit 16 is placed on the table 12 of the electron microscope. The integrated circuit may comprise solely one integrated circuit or a plurality of circuits produced on one and the same substrate. The circuit can be roughly positioned in relation to the path of the electron beam 7 by means of the table 12. The aforesaid identification of the position of the circuit 16 relative to the coordinate system x - y takes place when the circuit 16 is in alignment with the scanning range of the electron microscope.

This can be achieved in various alternative ways.

One method in this respect is to study the circuit manually on a presentation screen 3 while using a scanning electron beam, and to insert the position on the presentation screen of each of the identification points into the data processor 15, for example through a keyboard.

Alternatively, instead of a keyboard there can be used a marker which is capable of being moved across the screen with the aid of electronic control means connected to the data and which is manually moved to an identification point visually viewed on the screen. A signal is then sent to the data processor, which therewith senses the position of the marker on the screen and introduces this positional information into the memory store of the data processor. This marker may have the form of two mutually perpendicular intersecting lines.

This determination can, instead, be effected automatically by digitalizing the image appearing on the screen 3, by digitalizing in a separate device 23 the signal 24 produced by the detecting device 2 and effecting in the data processor 15 a so-called image comparison between firstly the output signal 31 from the digitalizing device 23 and secondly an image stored in the memory 25 associated with the data processor 15 of each of the identification points. When agreement prevails the data processor 15 evaluates the position of the electron beam 7 and feeds this positional information into the memory store 25. The position of the electron beam for each of the identification points is given in the coordinate system x - y, such as the coordinates ($x_1$, $y_1$), ($x_2$, $y_2$), ($x_3$, $y_3$) and ($x_4$, $y_4$).

An alternative method is one in which the electron beam is caused to sweep over the surface of the substrate and the position of the electron beam determined with the output signal from the detector 4, so as thereby to determine the position of the electron beam for given characteristic output signals from the detector 4 deriving from properties of the identification points.

In accordance with a preferred embodiment the position of the electron beam is determined upon irradiation of the identification point in question by irradiating with an electron beam an identification point which comprises an electronic component arranged, when irradiated with said beam, to send an electric signal to an electronic device, such as the data processor 15, the position of the electron beam being determined upon the occurrence of such a signal. The signal is sent therewith to the data processor 15, which therewith senses the position of the beam. This electronic component may be a diode forming part of the circuit.

In this alternative method, deflection of the electron beam is preferably controlled by means of the data processor and the deflection circuit 17, information concerning the position of the beam being found in the data processor. When the conventional control means 28 of the electron microscope is used to deflect the electron beam 7, it is necessary that the data processor 15 senses the control means 28, in order to determine the position of the electron beam. Scanning or sensing need not be effected over the whole circuit area, but can be confined to limited areas where the identification can be expected to be found.

Naturally, other alternative methods are conceivable.

The invention is in no way restricted to the method of determining the position of the identification points in the coordinate system x - y.

The position of the integrated circuit 16 in the x - y system is therewith known. The positions of the identification points and the selected nodes in the x' - y' system is known and stored in the memory store 25 of the data processor 15. Through coordinate transformation the positions of the selected nodes in the x - y system are expressed in the form of coordinates $(x_i, y_i)$, where i=5, 6, 7, . . . . n, the coordinates $(x_i, y_i)$ being fed into the memory 25 of the data processor 15.

The selected nodes are then inspected.

When carrying out this inspection in accordance with one embodiment, the data processor collects from the memory store 25 information concerning the position of the nodes $(x_i, y_i)$ and guides the electron beam 7 from node to node in a successive order, with the aid of the deflecting circuit 17. When the electron beam irradiates one node, the output signal 10 obtained on the detector 4 is compared in the data processor with information contained in the memory store 25 relating to that voltage level which shall prevail in the node in question at the prevailing voltage applied to the circuit 16. Thus, the data processor also controls the voltage applying circuit 13 in response to information contained in the memory store 25 with respect to the voltage to be applied to the circuit 16 when a given node is inspected.

Thus, this comparison discloses whether the node in question has the correct voltage level or not.

According to one embodiment, the data processor is programmed to solely ignite the electron beam 7 through the control of the ignition circuit 20, when the deflecting devices of the electron beam are activated in a manner to cause the beam to irradiate a node. The electron beam 7 is then extinguished and brought into alignment with the next node, whereafter the beam is ignited, and so on. This embodiment is particularly applicable when the circuit 16 or certain areas thereof is, or are, sensitive to electron irradiation.

In accordance with another embodiment, the electron beam 7 is caused to sweep along mutually parallel paths 27, over its scanning range 26 in a conventional manner. It will be understood that the paths 27 have a narrower interspacing than that shown in FIG. 4.

The scan made by the electron beam is preferably controlled by the data processor. According to this embodiment the data processor will preferably only sense the output signal 10 from the detector 4 when the electron beam is in a position such as to irradiate a selected node whose coordinates are stored in the memory store 25, as mentioned above. In this case, the load placed on the data processor is smaller than when it is adapted to sense or detect the output signal 10 continuously. The data processor carries out a comparison in accordance with the aforegoing with respect to the voltage level of the node in question each time the output signal is detected.

By means of the present invention, in which the circuit 16 remains stationary and the electron beam is moved from node to node, it is possible to read more than 10,000 nodes per second. It is quite evident that the present method is highly effective compared with methods utilizing mechanical notations. The efficiency of the present method is so high as to enable whole circuits incorporating highly complex patterns to be sensed in a few seconds. The method also enables one and the same node to be sensed when different voltages are applied to the circuit, therewith also enabling functional checks to be carried out.

The nodes to be sensed and their coordinates $(x'_i, y'_i)$ are suitably determined with the aid of the micromasks used to produce the circuit 16 in question. These masks are normally found stored in the data storage, from which the requisite coordinate information can be collected and fed to the memory store 25. Information relating to the voltage level of each node selected when a given voltage is applied to the circuit is suitably obtained from the data used when designing the circuit 16 in question.

The result of an inspection carried out in accordance with the aforedescribed method is fed from the data processor to a suitable output means 30, such as a writer and/or a data store.

The above description discloses how an integrated circuit can be inspected. It will be understood, however, that the present invention can be used to inspect other object having detectable electrical properties. For example, different points on objects other than integrated circuits can be examined. Such other objects may comprise, for example, biological samples, such as biological cells.

Naturally, modifications can be made. For example, more than one electron beam can be used. Furthermore, in certain cases the electron beam can be caused to irradiate certain selected nodes or whole conductors or other components for the purpose of changing their properties.

In accordance with a further preferred embodiment in this context, the state of the circuit is changed permanently or temporarily prior to, during or after the aforesaid inspection. In this respect, irradiation of given parts or nodes of the circuit forms a stage in the aforesaid inspection, such as a manufacturing stage, or as a stage for rectifying faults in a manufactured circuit.

The invention is considered to incorporate all the modifications given by way of example and other corresponding modifications.

Thus, the invention is not restricted to the described and illustrated embodiments, and modifications can be made within the scope of the following claims.

I claim:

1. An improved method to be used for inspecting objects such as integrated circuits, or other objects, where the object is irradiated by means of an electron beam of an electron microscope and where a detector is caused to detect electrons emitted from the object said object having a voltage level property, to determine a voltage level property of the object in at least one point which is generated by said irradiation, and to provide an output signal corresponding thereto, the improvement being characterized in that the points (nodes) on the object (16) to be inspected, in a first step, are allotted coordinates $(x'_i, y'_i)$ in a coordinate system (x' - y') related to the object; the second step being that identification points on the object are determined for the object being inspected, these identification points also being allotted coordinates $(x'_i, y'_i)$; the third step being that the object (16) is placed in an electron-microscope type device (1); the fourth step being that the position of the coordinate system x' - y' in relation to a coordinate system x - y related to the electron microscope (1) is determined by determining the position of the identification points relative to the coordinate system x - y; the fifth step being that the electron beam (7) of the electron microscope is then deflected into alignment with and irradiates said points (nodes) in a successive order, voltage being applied to said object upon inspection of each of the selected points (nodes); the next step being that the output signal obtained from the detector (4) upon irradiation of each of the selected points (nodes) is compared with the voltage level to the associated irradiated node; and using a data processor (15) to effect a coordinated transformation from the coordinate system x' - y' to the coordinate system x - y, whereafter the data processor (15) is caused to control and move the electron beam (7) to the selected points (nodes) to be inspected.

2. A method according to claim 1, the improvement being further characterized in that the electron beam (7) is caused to ignite only when a selected point (node) is irradiated.

3. A method according to claim 1, when the object to be inspected is an integrated circuit, characterized in that the voltage applied to the integrated circuit (16) is applied by means of a voltage applying circuit (13) and that the output signal from the detector (4) is compared with a predetermined value relating to the voltage supply to the associated irradiated node.

4. A method according to claim 1, characterized in that the positions of the identification points are detected by sensing the position of the electron beam (7) when the detector (4) produces an output signal characteristic of the identification point being irradiated by the electron beam.

5. A method according to claim 1, characterized in that the positions of the identification points on the object are detected by producing on a presentation screen an image of the object (16) generated by re-emission of electrons from a scanning electron beam, and by visually studying the screen, and in that each of the positions of the identification points on the screen are fed to a data processor (15).

6. A method according to claim 1, the improvement being further characterized in that at least one of the positions of the identification points of said object are detected by determining the position of the electron beam when irradiating the desired identification point, where said desired identification point comprises an electronic component which, when irradiated with an electron beam, is adapted to deliver an electric signal to said data processor, which provides said determination of the position of the electron beam.

7. An improved method to be used for inspecting objects such as integrated circuits, or other objects, where the object is irradiated by means of an electron beam of an electron microscope and where a detector is caused to detect electrons emitted from the object, said object having a voltage level property to determine a voltage level property of the object in at least one point which is generated by said irradiation, and to provide an output signal corresponding thereto, the improvement being characterized in that the points (nodes) on the object (16) to be inspected, in a first step, are allotted coordinates $(x'_i, y'_i)$ in a coordinate system $(x' - y')$ related to the object; the second step being that identification points on the object are determined for the object being inspected, these identification points also being allotted coordinates $(x'_i, y'_i)$; the third step being that the object (16) is placed in an electron-microscope type device (1); the fourth step being that the position of the coordinate system x' - y' in relation to a coordinate system x - y related to the electron microscope (1) is determined by determining the position of the identification points relative to the coordinate system x - y; the fifth step being that the electron beam (7) of the electron microscope is then deflected into alignment with and irradiates said points (nodes) in a successive order, voltage being applied to said object upon inspection of each of the selected points (nodes); the next step being that the output signal obtained from the detector (4) upon irradiation of each of the selected points (nodes) is compared with the voltage level to the associated irradiated node; and the improvement being further characterized by detecting the positions of the identification points on the object by digitalizing a first image of the object (16) generated by emission of a scanning electron beam (7), and making a comparison with a second image of the identification points of said object stored in a data store (25), the position of the electron beam (7) being determined upon irradiation of the identification point when agreement is found between the compared first and second images.

8. An improved method to be used for inspecting objects such as integrated circuits, or other objects, where the object is irradiated by means of an electron beam of an electron microscope and where a detector is caused to detect electrons emitted from the object said object having a voltage level property, to determine a voltage level property of the object in at least one point which is generated by said irradiation, and to provide an output signal corresponding thereto, the improvement being characterized in that the points (nodes) on the object (16) to be inspected, in a first step, are allotted coordinates $(x'_i, y'_i)$ in a coordinate system $(x' - y')$ related to the object; the second step being that identification points on the object are determined for the object being inspected, these identification points also being allotted coordinates $(x'_i, y'_i)$; the third step being that the object (16) is placed in an electron-microscope type device (1); the fourth step being that the position of the coordinate system x' - y' in relation to a coordinate system x - y related to the electron microscope (1) is determined by determining the position of the identification points relative to the coordinate system x - y; the fifth step being that the electron beam (7) of the electron microscope is then deflected into alignment with and irradiates said points (nodes) in a successive order, voltage being applied to said object upon inspection of each of the selected points (nodes); the next step being that the output signal obtained from the detector (4) upon irradiation of each of the selected points (nodes) is compared with the voltage level to the associated irradiated node; and using a data processor (15) to effect a coordinate transformation from the coordinate system x' - y' to the coordinate system x - y, whereafter the data processor (15) follows the position of a reciprocating scanning electron beam (7) to the selected points (nodes) to be inspected.

* * * * *